United States Patent
Knape et al.

(10) Patent No.: US 6,974,577 B2
(45) Date of Patent: Dec. 13, 2005

(54) INACTIVATED BOVINE SCOURS VACCINES, PROCESSES AND METHOD OF PREVENTING BOVINE SCOURS

(75) Inventors: Kelly Knape, Larchwood, IA (US); Stephanie Dykstra, Parker, SD (US); Mary Tinant, Brandon, SD (US)

(73) Assignee: Novartris AG, Basel (CH)

( * ) Notice: Subject to any disclaimer, the term of this patent is extended or adjusted under 35 U.S.C. 154(b) by 575 days.

(21) Appl. No.: 09/776,787

(22) Filed: Feb. 4, 2001

(65) Prior Publication Data

US 2002/0155128 A1 Oct. 24, 2002

(51) Int. Cl.$^7$ ............................................. A61K 39/295
(52) U.S. Cl. ................ 424/201.1; 424/202.1; 424/203.1; 424/221.1; 424/247.1; 424/241.1; 424/215.1; 424/283.1; 435/236; 435/237
(58) Field of Search .......................... 424/201.1, 202.1, 424/203.1, 221.1, 247.1, 241.1, 215.1, 283.1; 435/236, 237

(56) References Cited

U.S. PATENT DOCUMENTS

| | | |
|---|---|---|
| 4,298,597 A | 11/1981 | Acres et al. |
| 4,636,385 A | 1/1987 | Plotkin et al. |
| 5,916,570 A | 6/1999 | Kapil |
| 6,083,512 A | 7/2000 | Roberts |

OTHER PUBLICATIONS

Mostl. et al., Zentralblatt Fur Veterinarmedizin. Reihe B, (Apr. 1988) 35 (3) 186–96.*

Castro, Anthony E., Veterinary Diagnostic Virology, pp. 92–96, Mobsy Year Book (1992).

Harper, David R., Virology, p. 24, BIOS Scientific Publishers Limited (1993).

Hasoksuz, M. DVM, PhD., S. Lathrop DVM, K Gadfield, L. Saif, PhD., "Isolation of bovine respiratory coronaviruses from feedlot cattle and comparison of their biological and antigenic properties with bovine enteric coronaviruses," American Journal of Veterinary Research, vol. 60, pp. 1227–1233.

House, J.A., "Economic Impact of Rotavirus and Other Neonatal Disease Agents in Animals", JAVMA, vol. 173, pp. 573–576 (1978).

Milane et al., "Characterization of Monoclonal Antibodies to the Hermagglutinin–Esterase Glycoprotein of a Bovine Coronavirus Associated with Winter Dysentery and Cross–reactivity to Field Isolates", Journal of Clinical Microbiology, vol. 35, pp. 33–40, (1997).

Castro, Anthony E., Veterinary Diagnostic Virology, pp. 126–130, Mobsy Year Book (1992).

K. Fukai, "Prevalence of Calf Diarrhea Caused by Bovine Group A Rotavirus Carrying G Serotype 8 Specificity", Veterinary Microbiology, vol., 66, pp. 301–311, (1993).

Harper, David R., Virology, p. 322, BIOS Scientific Publishers Limited (1993).

W. Lu, "Characterization of the Bovine Group A Rotavirus Strain Neonatal Calf Diarrhea Virus–Cody (NCDV–cody)", Journal of Clinical Microbiology, vol. 33, pp. 990–994, (1995).

* cited by examiner

*Primary Examiner*—Laurie A. Scheiner
(74) *Attorney, Agent, or Firm*—David L. Marks

(57) ABSTRACT

Inactivated scours vaccines for immunization and protection of bovine animals from disease caused by infection with bovine rotavirus and bovine coronavirus, which comprise and effective amount of at least one inactivated viral strain are described. Polyvalent inactivated vaccines further comprising an effective amount of an antigenic component which is protective against one or more additional pathogenic organisms or viruses are also disclosed. Said vaccines are prepared from one or more strains of rota- and coronavirus, *C. perfringens* Type C bacteria and *E. coli* bacteria, and combinations thereof. Preferably, a polyvalent inactivated vaccine is provided for parenteral administration. Passive immunity is achieved in neonatal calves via immunization of pregnant cows prior to birth.

65 Claims, No Drawings

INACTIVATED BOVINE SCOURS VACCINES, PROCESSES AND METHOD OF PREVENTING BOVINE SCOURS

FIELD OF INVENTION

The present invention relates to the general field of immunology, and specifically to veterinary vaccines against viruses and/or bacteria that are the causative factors in scours. More particularly, the invention relates to the propagation of scours-causing microbial isolates and subsequent inactivation thereof, to polyvalent vaccines containing the inactivated scours-causing agents and to the use of such vaccines to vaccinate bovine animals. The inactivated vaccines of this invention are particularly useful for vaccinating pregnant cows. This application, thus, describes neonatal scours vaccines consisting of inactivated virus isolates and/or toxoid combinations.

BACKGROUND OF THE INVENTION

The principle of vaccination is based on two key elements of adaptive immunity, namely specificity and memory. Memory cells allow the immune system to mount a much stronger response on the second encounter with antigens. This secondary response is both faster to appear and more effective than the primary response. The aim in vaccine development is to alter a pathogen or its toxin in such a way that they become innocuous without losing antigenicity. This is possible because antibodies and T cells recognize particular parts of antigens, the epitopes, and not the whole organism or toxin. For example, a toxin produced from a bacterium may be modified, e.g. by formalin treatment, so that it retains its epitopes but loses its toxicity. The resulting toxoid is used as a vaccine. Viruses may be attenuated and/or inactivated so that they retain their antigenicity but lose their pathogenicity.

Neonatal calf diarrhea, also known as calf scours and calf enteritis, is a serious, contagious disease caused by a variety of organisms, including *Escherichia coli, Clostridium. perfringens,* rotavirus and coronavirus, often in combination and/or with other bacteria, viruses and intestinal parasites. Although antibiotics given to scouring calves can help control bacteria, over-relying on them is ineffective, as they are ineffective against viral or parasitic infections. Moreover, antibiotics reduce the number of beneficial bacteria in the gut, and use over extended periods can lead to microorganisms becoming resistant to antimicrobial drugs used for treatment, e.g. antibiotic resistant bacteria—particularly *E. coli*.

For many years, extensive research has been directed toward the preparation of safe and effective veterinary scours vaccines. A number of scours vaccines are currently marketed for use in cattle and other animals. These vaccines are generally classified as attenuated or inactivated, referring to the final vaccine product containing a modified live virus or a killed virus. The scours veterinary vaccines currently marketed include, e.g., ScourGuard™, and are known to be of limited efficacy.

Calf scours, the leading cause of economic loss and death in calves, is usually caused by a combination of factors. Hence, a vaccine to prevent scours should include protection against the four most common causes of scours: coronavirus, rotavirus, *E. coli* and *Cl. perfringens* Type C. Attaining high levels of antibody in the colostrum through the use of potent vaccines has proven extremely effective in preventing calf scours. The most effective vaccination program is one in which the level of antibodies in the dams' system peaks at or just prior to calving, providing maximum protection to the calf via the colostrum. Historically, immunization required vaccines to be given within two weeks to a month pre-calving, and required two and sometimes three doses. Vaccination of cows close to calving is a management problem that can overly stress both the cow and the fetus. The vaccines of this invention provide maximum protection while minimizing such stress.

Bovine coronavirus (BCV) causes both enterocolitis and respiratory tract infections in calves and adult cattle. In some instances, the diseases are referred to as calf diarrhea, calf scours or calf enteritis, and winter dysentery in adult cattle. Coronavirus effects calves as soon as their second week of life but can effect older calves as well. Heretofore, virus vaccines have been prepared by extensive passaging of the virulent virus. These known vaccines have proven to be clinically ineffective against many wild-type BCV infections. Coronavirus causes one of the most severe viral diseases of neonatal calves and may completely destroy the villi of the intestine. Evidence also suggests that some forms of Coronavirus contribute to respiratory disease. Coronavirus causes severe disease alone, but is influenced by coinfections with other enteropathogens. That is, concurrent infection with *E. coli* and/or rotavirus often complicates the disease process. Unlike bovine rotavirus, only one serotype of bovine coronavirus is known.

Rotaviruses (RV) cause acute gastroenteritis, malabsorptive diarrhea, and dehydration in severe cases. The disease severity is influenced by coinfections with other enteropathogens. Rotavirus is recognized as a distinct entity and is divided into six groups based upon how the proteins on its outer surface behave antigenically. Two of those groups—Group A and Group B—commonly infect cattle; within those groups, a number of different serotypes have been identified. The most common G serotypes of group A rotaviruses affecting calves are G6 and G10. G8 may also be emerging as a prevalent genotype. Three P serotypes have been identified in calves with scours: P6(1), P7(5) and P8(11).

The two non-viral pathogens addressed by this invention include *Escherichia coli (E. coli)* and *Clostridium perfringens* Type C *(Cl. perfringens)*. *E. coli* pathogens are commonly found in the gut and the manure of healthy cattle, resulting in most calves being exposed shortly after birth. These bacteria attach to the lining cells of the intestine by means of hair-like projections called pili. These attached bacteria produce toxins that cause the intestine to secrete large amounts of fluid, which can result in scours, dehydration and death.

*E. coli* is divided into antigenic types based on adhesiveness factors on the surface of the cell wall and its ability to produce various toxins. Specific pilus formation appear to be controlled by DNA outside the chromosome. This DNA replicates autonomously and can thus be transferred from one *E. coli* to the next, often resulting in increased virulence and mutations in the field.

*Cl. perfringens* Type C commonly inhabits soil as well as the intestinal tracts of healthy cattle, meaning calves are easily exposed and infected. Changes in the environment of the calf's stomach allow the Type C organisms to grow, producing enterotoxins that cause severe symptoms and high death losses.

The vaccines of the present invention, accordingly, are prepared from virus and/or bacteria originally obtained in the field, and more specifically, are prepared from various combinations of bovine coronavirus, bovine rotavirus, *E. coli* and *Cl. perfringens* Type C originally obtained in the field. That is, they were obtained by collecting biological samples and identifying/isolating the specific strains.

Vaccines must contain the correct serotypes of the organisms responsible for scours in order to prevent it. Although available scour vaccines are carefully produced to insure they contain the organisms claimed on the label, there are differences in the number of serotypes in the products that are available. The best vaccine is one that demonstrates immunity in calves challenged with specific serotypes of the important scours-causing organisms.

Accordingly, there is a real and unsatisfied need in the art for new treatment modalities for cattle at risk for scours-causing infections, both in terms of a more effective and broader coverage vaccines. The novel scours vaccines disclosed herein comprise viruses that are propagated on cell cultures and an effective vaccine is prepared by inactivating the virus after it has been grown on other cell cultures. Therefore, this invention consists of polyvalent vaccines effective against neonatal calf scours comprising one or more inactivated viruses, may further comprise one or more bacterial strains, and methods of preparing and administering these vaccines.

SUMMARY OF THE INVENTION

This invention relates to bovine scours vaccines, methods of preparing vaccines and methods of using the vaccines. These vaccines are used in healthy pregnant cattle as an aid in the prevention and control of disease in calves caused by bovine rotavirus, bovine coronavirus, *Clostridium perfringens* Type C and K99 piliated *Escherichia coli*. This invention is useful in and applicable to all conventional uses of vaccines, in cattle and others, and derivatives thereof, but is not intended to be limited to these uses.

This invention also comprises a method of protecting newborn calves against scours by administering to pregnant cows prior to birth of said calves a vaccine prepared according to this invention.

In one embodiment of the invention, a combination bovine rotavirus and bovine coronavirus vaccine is described, said vaccine conferring heterologous coverage for multiple rotavirus and coronavirus serotypes. That is, it includes three distinct field isolates of bovine rotavirus, Group A, that encompass all of the common G and P serotypes.

In another embodiment, a combination vaccine comprising *E. coli* and *Cl. perfringens* bacterin-toxoid in combination with bovine coronavirus and bovine rotavirus is disclosed.

Yet, another embodiment, provides vaccines comprising only bovine coronavirus in combination with *E. coli* and *Cl. perfringens* bacterin-toxoid.

Heretofore, polyvalent scours-causing agents have not been isolated, propagated and inactivated to produce vaccines, i.e., having fractions comprising multiple strains of the virus and/or bacteria. The present invention comprises the preparation of safe and highly effective polyvalent vaccines for immunization of pregnant cows in order to provide passive immunity to neonatal calves against scours.

The vaccine of this invention is administered parenterally, preferably by intramuscular or subcutaneous injection, in one or more doses. Preferably, a single 2.0 ml dose of vaccine containing inactivated virus-containing fluids, and may further comprise inactivated *Cl. perfringens* Type C fluids and inactivated *E. coli* fluids, combined with a suitable adjuvant, and may be further combined with a carrier and/or stabilizer, is administered. Preferably, pregnant cows should be vaccinated one time, intramuscularly, approximately 40 days or 8–10 weeks prior to calving. The virus fraction of the vaccination must be repeated in 6 weeks. With subsequent pregnancies, a single revaccination 8–10 weeks prior to calving is required.

The coronavirus used to prepare the inactivated virus vaccines of this invention is the Mebus strain having ATCC Accession No. VR-874. The bovine rotavirus used in the preparation of these vaccines includes three distinct rotavirus strains, including Cody 81-4 having ATCC accession number PTA-5955, G type 10B223 having ATCC accession number PTA-5956 and B641 having ATCC accession number PTA-5957 (all three strains are deposited according to the Budapest Treaty with the American Type Culture Collection, 10801 University Blvd., Manassas. Va., 20110-2209); the former two available from and being maintained at the Animal Disease Research and Diagnostic Laboratory, Brookings, S. Dak. by David Benfield, the remaining strain being maintained at Texas A & M by Dr. Gerald Woode, Dept. of Veterinary Medicine, College Station, Tex. Four *E. coli* strains comprise the *E. coli* fraction of the present vaccines, said *E. coli* strains including B41 having ATCC accession number PTA-5951, B42 having ATCC accession number PTA-5952, B44 having ATCC accession number PTA-5954, and B117 having ATCC accession number PTA-5953 (all four strains are deposited according to the Budapest Treaty with the American Type Culture Collection, 10801 University Blvd., Manassas, Va., 20110-2209) was obtained from the Animal Disease Research and Diagnostic laboratory, Brookings, S.Dak. The remainder of the *E. coli* strains were obtained from the *E. coli* Reference Center, Pennsylvania State University, University Park, Pa. All of the *E. coli* strains are maintained at the *E. coli* Reference Center in Pennsylvania. The *Cl. perfringens* Type C, is a strain identified as having genotype C, and is an alpha and beta toxin producter, strain GL47, having ATCC accession no. PTA-3000. It was isolated from a field case by Grand Laboratories, Inc. and is maintained at Grand Laboratories, Larchwood, Iowa.

To prepare the viral fractions of these inactivated vaccines, the viruses are cultivated in cell culture at from about 35° C. to about 39° C., preferably about 37° C. The virus is inactivated with an inactivating agent which does not destroy the virus particles or antigenicity according to standard methods known to the art.

To prepare the vaccine of this invention, the inactivated scours causing agents are combined with an adjuvant., A suitable carrier and/or a stabilizer according to standard, known in the art methods may be combined therewith. Any known adjuvant that enhances the antigenicity of the vaccine may be used, preferably an oil based, adjuvant such as Xtend® III (Grand Laboratories, Inc., Larchwood, Iowa).

It has been found that a single 2.0 ml intramuscular vaccination with the inactivated scours vaccine of this invention, the fractions thereof having bovine coronavirus and bovine rotavirus titers of $10^4$ to $10^9$ $FAID_{50}$, *Cl. perfringens* antigen levels of 400 to 1000 CPU and *E. coli* antigen levels of $10^4$ to $10^{10}$ cfu per field dose elicits significant serological responses in 100% of vaccinated cattle. At 10 weeks post vaccination, calves from these cattle remained protected against challenge with virulent virus which effected unvaccinated controls.

The inactivated scours vaccines of this invention have been licensed for use in cattle by the U.S. Department of Agriculture, Animal and Plant Health Inspection Services on 4 Feb. 2000 and 7 Feb. 2000 and are commercially available under the names ScourBos 4™, ScourBos6™ and ScourBos9™ from Grand Laboratories, Larchwood, Iowa.

Other features and advantages of the present invention will become apparent from the following detailed description.

DETAILED DESCRIPTION OF THE PREFERRED EMBODIMENTS

It is to be understood that both the foregoing general description and the following detailed description are exemplary and explanatory only and are not restrictive of the invention as claimed.

The vaccines provided herein provide ideal coverage under real-world conditions. Requiring a limited number of doses—one per cow annually after the first year of immunization—and they provide broad-spectrum coverage against multiple serotypes of rotavirus plus coronavirus. Three field isolates of Group A bovine rotavirus are included, encompassing all of the common G and P types encountered in the United States. These vaccines show consistent characteristics and confer consistent protection.

This invention is directed to the isolates, cell cultures, toxoids and vaccines produced therefrom, and may include variants, mutants and modifications of the same and/or similarly characterized pathogenic agent. This invention may also relate to the use of such isolates and vaccine combinations in producing other vaccines, e.g., combination with other monovalent or polyvalent vaccines.

The instant invention provides vaccines having superior efficacy in relation to those currently available.

Briefly, the general production of an inactivated vaccine from virus begins by finding a pathogenic strain of said virus. To do so, a biological sample is obtained from sick calves and submitted to a diagnostic lab for testing, e.g., serotype determination and field strain identification. The strain is then cultured and inactivated. The preferred inactivating agent for the viruses is β-propiolactone (BPL), as it does not alter the antigen as much as other agents, such as formalin, are prone to do. Next, a dosage is determined, i.e., 1, 2 or 5 ml, and efficacy studies performed by vaccinating and subsequently testing efficacy by direct viral challenge and/or blood testing for seroconversion which correlates with protection.

The development of injectable bacterin-toxoid biologicals for immunological protection is well known in the art.

Key improved characteristics by which these vaccines may include, e.g., unique and multiple serotype rotavirus isolates, unique methods of culturing, and all vaccine fractions Combinable with an oil based adjuvant. However, one skilled in the art can readily obtain other appropriate strains from suitable depositories, academic or commercial sources. The necessary deposits have been made under the Budapest Treaty and in accordance with MPEP §608.01(p) and 37 C.F.R. §§1.801–1.809, with the American Type Culture Collection, 10801 University Blvd., Manassas, Va., 20110-2209 and assigned ATCC accession number PTA-3000. All restrictions on the availability to the public of the deposited material identified herein will be irrevocably removed upon the grant of a patent on this application, the culture(s) will be maintained for a period of 30 years from the deposit date, or at least five years after the most recent request for a sample, whichever is longer; and the deposit will be replaced if viable samples cannot be dispensed by the depository.

In order to prepare the vaccines of this invention, the strain is first cultivated and then killed, e.g., chemically inactivated, and an adjuvant added for enhancement of immunogenicity. Any of the known adjuvants may be used, including oil based adjuvants, Freund's incomplete adjuvant, alginate adjuvant and aluminum hydroxide adjuvant, but preferably an oil based adjuvant such as Xtend® III. The vaccines are used in the liquid state. For optimum results, pregnant cows should be immunized approximately 40 days (~8–10 weeks) prior to calving, followed 6 weeks later with a the appropriate viral booster, and a single annual booster thereafter that follows the 8–10 week before calving guideline. When protecting calves by administering vaccine to the pregnant cow, the present vaccine fractions should have at least a rotavirus titer of $10^7FAID_{50}$, at least a coronavirus titer of $10^{7.5}FAID_{50}$, at least a *Cl. perfringens* antigen level of 621 CPU and at least an *E. coli* antigen level of $10^9$ cfu, and preferably, a rotavirus titer of $10^{7.5}FAID_{50}$, a coronavirus titer of $10^8FAID_{50}$, a *Cl. perfringens* antigen level of 700 CPU and an *E. coli* antigen level of $10^{9.5}$ cfu. The vaccines should be administered parenterally, preferably intramuscularly.

The following examples describe the preparation of the inactivated vaccines in accordance with the invention, and moreover describe a manner of use thereof, but are not to be construed as limiting the scope thereof.

Preparation of the Inactivated Vaccines

The viral agents described herein are propagated on cell lines comprising fetal bovine kidney cells. The virus may also be propagated on cells from other tissues or cell lines of bovine or other origin. Bovine rotavirus is cultured on monolayer cell cultures that are prepared by known methods and inoculated with the viral agent. Generally, monolayer cultures are washed with a balanced salt solution (BSS) and then viral inoculum is added and allowed to be absorbed for several hours, e.g., 2 hours at 37° C. A maintenance medium of balanced salt solution including antibiotic is added and the culture is incubated at approximately 30–40° C., preferably 37° C., for approximately 1–10 days. The virus is then inactivated.

An effective inactivated vaccine is prepared after inactivating the virus. In general, this preparation is accomplished by propagating the virus on, e.g., fetal bovine kidney cells, until an adequate titer is obtained. The virus is then inactivated by treating it at approximately 20–40° C. with an inactivating agent known in the art, e.g., formalin, ethyleneimine derivatives, ultraviolet radiation or heat, and preferably β-propiolactone, for such a length of time and/or concentration of inactivating agent as to effectively inactivate the virus. These procedures and their details are well known in the art. An adjuvant may be added to enhance the antigenicity. That adjuvant may be any of those known in the art, e.g., Freund's incomplete, alginate, aluminum hydroxide gel, or potassium alum, preferably an oil based adjuvant.

Bovine coronavirus is cultured in a suspension cell culture that is prepared by known methods and inoculated with the viral agent.

In the rota-coronavirus embodiment of the invention, a single coronavirus isolate is combined with three rotavirus isolates to create a polyvalent combination vaccine. The coronavirus used herein was isolated from a calf with diarrhea. It was passaged 36 times prior to master seed preparation, at which time the isolate was passaged 3 times in MDBK cells. The rotavirus strains identified as Cody 81-4 and B641 were isolated from a calf with diarrhea and passaged 7 and 29 times, respectively, prior to master seed preparation, at which time the Cody 81-4 isolate was passaged 1 time in MA-104 cell line and the B641 isolate was passaged twice in MA-104 cells. The G type 10B223 rotavirus strain was passaged 14 times prior to master seed preparation at which time the isolate was passaged 3 times in MA-104 cells.

The embodiment of the combination vaccine described herein comprising rotavirus and coronavirus combination preferably comprises equal parts, by volume, of each of the three strains of rotavirus isolates and equal volumes of each of the two viruses, such that the inactivated viral fluids comprise 44.4% of the total volume. In a preferred embodiment, the remainder of volume, 55.6%, is comprised of a oil based adjuvant.

More specifically, for the culture of viruses for the vaccines of the instant invention, cells are grown in tissue culture medium containing one of the following sterile tissue culture nutrient sera and pH adjusted to 7.2 (±0.1) with 10N sodium hydroxide:

| Serum type | % serum |
| --- | --- |
| Iron fortified calf | 7.5 |
| Fetal bovine | 5.0 |
| Bovine calf | 9.0 |
| Equine | 10.0 |

For virus propagation, infected cells are grown in tissue culture medium containing 2.0% sterile tissue culture nutrient serum and trypsin solution, the percentage of which is determined by testing the endpoint dilution and the next two 2 fold dilutions for virus propagation to determine the working dilution of the trypsin solution. For example, if the first dilution that shows no toxicity is 1:64, then the dilutions for the Virus Validation will be 1:64, 1:128 and 1:256. The use dilution is that dilution which shows the highest geometric mean virus titer. The specific methodology of an optimization assay is known to the skilled artisan, i.e., within the ambit of virus research and development. Master seed and production virus is propagated in roller bottles on an apparatus rotating at 12 (±3) revolutions per hour. Seed cultures, both frozen and lyophilized, are stored at at least −30° C.

In use, frozen seed virus fluids of known titer are rapidly thawed to about 35–39° C., diluted with medium so as to contain the required amount of virus, and inoculated onto the cells at the following target multiplicity of infection (MOI) rates:

| Microorganism | Isolate | Culture Type | MOI range ($\log_{10}$) |
| --- | --- | --- | --- |
| B. rotavirus | Cody 81-4 | monolayer | 2.5–3.1 |
| B. rotavirus | G type 10B223 | monolayer | 2.4–3.0 |
| B. rotavirus | B641 | monolayer | 2.4–3.0 |
| B. coronavirus | Mebus | suspension | 1.7–2.3 |

Monolayer cultures contain 0% serum. Actual MOIs are determined by growth studies to optimize the virus titers. Cell propagation is achieved by dispersing confluent monolayers of cells with Trypsin Solution, harvesting them in a common container and counting. Virus propagation for rotavirus is achieved by adding virus to confluent monolayers, allowing it to adsorb for approximately 1.5 hours and refeeding with virus propagation medium according to known methodology.

Coronavirus propagation is affected by adding virus to suspended cells, allowing it to adsorb for approximately 1.5 hours, adding to the virus propagation medium and dispensing into roller bottles. Infected cells form monolayers. All cultures are incubated at approximately 35–39° C., preferably 37° C., for 1–10 days on a roller bottle apparatus.

The infected cell cultures in the roller bottles are disrupted by one freeze (≦−20° C.) thaw (35–39° C.) cycle prior to harvest. Cultures are harvested after ≧60% CPE (cytopathic effect) is observed. Actual harvest times are determined by growth studies to optimize the virus titers, but generally fall within the 1–7 day range for rotavirus and 2–10 day ranges for coronavirus. Fluids to be harvested, i.e., those containing the disrupted cells, are aseptically pooled in a sterile reservoir and assay samples are collected therefrom. The minimum acceptable harvest titer for rotavirus and coronavirus is $10^{4.0}$FAID$_{50}$ per ml, preferably $10^{7}$FAID$_{50}$ per ml and $10^{7.5}$FAID$_{50}$, respectively.

Bovine rotavirus fluids, preferably, are inactivated with β-propiolactone to a final concentration of 0.2% and incubated at approximately 35–39° C., preferably 37° C., for approximately 48–54 hours under constant agitation. The pH is adjusted to 7.1 (±0.2) with sterile 10N sodium hydroxide. The inactivated virus fluids are then stored at approximately 2–70° C.

Bovine coronavirus fluids are also preferably inactivated with β-propiolactone to a final concentration of 0.1% and incubated at approximately 35–39° C., preferably 37° C., for approximately 22–31 hours under constant agitation. The pH is adjusted to 7.1 (±0.2) with sterile 10N sodium hydroxide. The inactivated virus fluids are then stored at approximately 2–70° C.

The vaccines of this invention may further comprise one or more preservatives and adjuvants, e.g., preservatives may include Amphotericin B Solution to a final concentration of 2.5 mcg/ml, penicillin/streptomycin to a final concentration of 30 units/30 mcg/ml and/or thimerosal to a final concentration of 1:10,000. Completed vaccines are emulsified and comprise 55.6% adjuvant. The inactivated fluids are combined and the pH is adjusted to 7.1 (±0.2) with sterile 10N sodium hydroxide. The inactivated fluids and adjuvant are emulsified using, e.g., a Ross homogenizer (Charles Ross & Son, Haupauge, N.Y.) at 18 psi resulting in a flow rate of 20–22 liters per minute. Stabilizers are preferably not included in the vaccines of this invention. Sterile preservatives are aseptically added to the viral fluids prior to emulsification and sterile antifoam is added to the aqueous pools to a completed product concentration of 0.06%. Inactivated viral fluids may be concentrated by ultrafiltration.

Alternative Combination Embodiments

A further aspect of this invention is the preparation and use of combination polyvalent vaccines comprising vaccinal amount of one or more of the adjuvanted inactivated scours causing agents described herein and one or more additional pathogenic entities, e.g., one or more bacteria fractions. For example, vaccines comprising vaccinal amount of coronavirus and/or rotavirus combined with E. coli and Cl. perfringens may be prepared. An example of such a polyvalent bovine vaccine encompassed by this invention comprises, proportionately, approximately 22.7% inactivated viral fluids, inactivated Cl. perfringens type C fluids approximately 7.6%, approximately 14.1% inactivated E. coli fluids and oil adjuvant comprising 55.6% of total vaccine volume. More particularly, each 2 ml dose of prepared vaccine contains at least $10^{7}$FAID$_{50}$ of each bovine rotavirus isolate Cody 81-4, G type 10B223 and B641, $10^{7.5}$FAID$_{50}$ of bovine coronavirus, 621 CPU of Cl. perfringens Type C, and $1.6 \times 10^{9}$ cfu of E. coli strains B41 and B44, and $1.0 \times 10^{9}$ cfu of E. coli strains B42 and B117.

An additional embodiment of the invention is the combination vaccine of a vaccinal amount of bovine coronavirus further comprising a vaccinal amount of *Cl. perfringens* Type C and *E. coli* bacterin-toxoid, wherein the coronavirus is prepared as described supra and combined with the *Cl. perfringens* Type C isolate and four *E. coli* isolates previously identified herein. Each of the *E. coli* isolates was isolated from a calf with diarrhea and a master seed established from said isolate. The proportions of each of the *E. coli* isolates contained in the total *E. coli* fraction is, preferably, about 25%. Hence, proportionately the inactivated viral fluids comprise about 22.7%, inactivated *Cl. perfringens* type C fluids about 7.6%, inactivated *E. coli* fluids 14.1% and oil adjuvant 55.6% of total vaccine volume. More particularly, each 2 ml dose of vaccine contains at least $10^{7.5}$FAID$_{50}$ of bovine coronavirus, 621 CPU of *Cl. perfringens* Type C strain GL47, and $1.6\times10^9$ cfu of *E. coli* strains B41 and B44, and $1.0\times10^9$ cfu of *E. coli* strains B42 and B117.

All of the embodiments of the invention have a longer duration of protective effects that those currently available on the market, as well as an extremely low incidence of injection site reaction, both intramuscular and subcutaneous. The polyvalent vaccines of this invention are administered parenterally, preferably by intramuscular injection.

Use of Inactivated Vaccines

These inactivated vaccines are administered parenterally in doses of 1 to 5 ml, preferably 2.0 ml, to pregnant cows approximately 40 days prior to calving, to provide protection from infection with the one or more virus and/or infection with one or more bacteria of which the vaccine is comprised.

The inactivated polyvalent vaccines were tested for effectiveness by administering the vaccine to pregnant cows approximately 40 days prior to calving. At a later time, the calves were challenged by inoculation with virulent virus and/or bacteria. The results of these tests are summarized in Tables 1–3.

Vaccination and Challenge

I. Bovine Coronavirus Immunogenicity

Calves born to heifers vaccinated with the inactivated polyvalent combination vaccine of this invention comprising bovine rotavirus, bovine coronavirus, *Cl. perfringens* Type C-*E. coli* bacterin-toxoid were protected from a virulent challenge with bovine coronavirus. Those calves responded with a protective serologic responses to *Cl. perfringens* Type C and the K99 pilus of *E. coli*, as well. A single dose of vaccine is shown to protect as well as two doses.

Sixty seven Angus heifers, weighing between 500 and 800 pounds were randomly assigned into 3 test groups and pastured together prior to calving. Three vaccines were prepared for this challenge: 1) combination vaccine including rotavirus, coronavirus, *Cl. perfringens* and *E. coli* fractions and having a coronavirus an antigenic level of $10^{7.5}$FAID$_{50}$ per 2 ml dose ("VP-760"); 2) combination vaccine including rotavirus and coronavirus without the bacterial fractions in a 2 ml dose ("VP-761 "); and, 3) vaccine including *Cl. perfringens* and *E. coli* without the viral fractions (1 ml dose) ("BP-635"). All animals were vaccinated with a dose of one of the three vaccines, approximately 8 weeks prior to calving. Twenty one heifers received a second viral dose approximately 6 weeks thereafter.

At the time of the second vaccination, antibacterial treatment commenced. In particular, Aurea S700 2G was mixed in the feed at a rate to deliver 350 mg sulfamethazine and chlortetracycline per heifer per day until parturition. Individual calves received 5 ml Naxcel™ orally at birth, followed by 5 ml Aquacillin™ intramuscularly at 1- and 2-days post parturition. All calves received 5 ml of Naxcel™ orally at day 17 post parturition.

After calving, cow-calf pairs were separated from the heifers and housed together until challenge. On day 3 post parturition, the cow-calf pairs were again separated and housed together for a 14-day observation period. The off test pairs were housed together in a separate area for at least 21 days post challenge.

Calves were challenged at 3-days post parturition with challenge bovine coronavirus (UNL 4-17-92) that was obtained from and is maintained by Dr. Gerald Duhamil at the University of Nebraska, Lincoln, Nebr. Prior to challenge, challenge doses of 2.5 ml or 5 ml virus were diluted in 5 ml Minimum Essential Medium (MEM) containing antibiotics for total volume doses of 7.5 ml and 10.0 ml, respectively. The challenge dosage consisted of administration of 1 ml into each nostril and the remainder of the dosage delivered orally to the calf prior to immediate return to the cow.

Fourteen animals were not used in the study for various reasons, none of which effected the results of the immunogenicity study. Post challenge monitoring included clinical observation and scoring for fecal consistency, depression and dehydration for 14-days: fecal consistency is scored on a scale of 0–3, where 0=normal and 3=severe watery scours; dehydration is scored on a scale of 0–2, where 0=normal and 2 =sever, eyes sunken; and, depression is scored on a scale of 0–3, where 0=normal and 3=sever, unable to stand, near death.

Fecal samples were obtained from each animal daily for 14 days by inserting and withdrawing a culturette swab approximately 2 inches into the rectum. Each swab was placed in 5.0 ml MEM with antibiotics, incubated at approximately 20–25° C. for about an hour, then centrifuged at 600×g for 20 minutes. Supernatant was poured off and frozen at −60° C. In addition, approximately 10 ml of fecal material was collected at challenge day 0, 7 and 14, and frozen at −20° C.

Blood samples and colostrum were collected from heifers at parturition and from the cow and the calf at challenge days 0, 7 and 14 and frozen at −20° C. Serum and colostrum from the heifers vaccinated with vaccine VP-760, and their calves, were tested for specific antitoxin titers using the procedures described in 9 CFR §113.111(c). Serum from pre-vaccination and each sampling were accordingly pooled and tested for the presence of antitoxin titers, as were the colostrum samples. Serum were also titered for K99 antibodies using ELISA methodology.

Serum and colostrum from the heifers vaccinated with VP-760, and their calves, were tested for specific antitoxin titers using the procedures described in 9 C.F.R. §113.111 (c). A pool of pre-vaccination serum was tested for the presence of antitoxin titers at 1 International Unit (IU) for *Cl. perfringens* Type C. The efficacy of the *Cl. perfringens* fraction of these vaccines was demonstrated by the specific antitoxin level passively acquired in nursing calves from heifers vaccinated with one dose of VP-760 exceeding the requirements in 9 C.F.R. §113.111(c) at 3 and 10 days of age. Additionally, VP-760 passed the rabbit potency test.

Serum from the heifers vaccinated with VP-760 were titered for K99 antibodies using an ELISA serology test. The K99 serology assay indicated that 80 percent of the calves nursing dams with a titer of 3.12 (Log Base 2) at parturition are expected to be protected, and which demonstrated 100% protection in calves nursing dams with a Log Base 2 titer of 4 or greater at parturition. The K99 antibody titers elicited by cattle vaccinated with VP-760 were ≧4 (Log Base 2) for 82.7% of the heifers at parturition.

The mortality rate in the control animals was 30%. None of the vaccinated animals died, regardless of which vaccination schedule they received. Challenged control calves had softer than normal stools and began to show signs of dehydration as early as day-2 post challenge. However, there was no significant difference between the calves challenged with 2.5 ml and 5.0 ml in the onset or overall severity at the challenge.

Clinical signs in calves born to vaccinated heifers were significantly less severe (p=0.000) than those in the control calves. Control calves had clinical scores that were four times the 1 dose vaccinated animals' scores, and twice the 2 dose vaccinated animals' scores. However, the clinical scores from 1 dose vaccinated animals were not significantly different than those from 2 dose vaccinated animals (p=0.134).

Vaccinated calves gained an average of 3.95 lbs. per day more than challenge control calves in the first week post challenge, and 0.84 lbs. per day more in the second week post challenge. Vaccinates weighed an average of 30 lbs. per calf more than controls by day 14 post challenge. Overall, the control calves had clinical scores three-times higher than vaccinated calves, that data summarized in Table 1.

TABLE 1

| | AVERAGE CLINICAL SCORE | | |
|---|---|---|---|
| | CHALLENGE DOSE | | TOTAL OF BOTH |
| TEST GROUP | 2.5 | 5.0 | CHALLENGE GROUPS |
| one vaccine | 14.86 | 7.40 | 11.75 |
| | (n = 7) | (n = 5) | (n = 12) |
| two vaccine | 25.22 | 14.50 | 20.18 |
| | (n = 9) | (n = 8) | (n = 17) |
| total vaccine | 20.69 | 11.77 | 48.23 |
| | (n = 16) | (n = 13) | (n = 23) |
| Control | 45.30 | 50.67 | 48.23 |
| | (n = 10) | (n = 13) | (n = 23) |

The above data establishes a minimum antigenic level of $10^{7.5}FAID_{50}$ per 2 ml dose when administered subcutaneously as either a single or two dose regiment. Moreover, the data demonstrates the lack of interference on the bovine coronavirus fraction by the other fractions comprising the vaccine in toto.

All statistical analysis was performed using SYSTAT for Windows, version 5.02, clinical scores were evaluated using the Analysis of Variance (ANOVA) test and mortality rates were evaluated by the Fishers Exact test.

II. Bovine Rotavirus Immunogenicity

Calves born to heifers vaccinated with the inactivated polyvalent combination vaccines of this invention comprising bovine rotavirus, bovine coronavirus, *Cl. perfringens* Type C-*E. coli* bacterin-toxoid were protected from a virulent challenge with bovine rotavirus. More specifically, calves born to heifers vaccinated with either one or two doses were protected from a virulent challenge with viral protein 4 (P types 1 and 5) and viral protein 7 (G types 6 and 8) of Type A bovine rotavirus.

Seventy one Angus heifers, weighing between 500 and 800 pounds, were randomly assigned into 4 groups: 2 dose vaccinates, 1 dose vaccinates, controls and ScourGuard® vaccinates. The ScourGuard® vaccinates received two, 2 ml doses intramuscularly at 4 and 2 weeks prior to calving, in accordance with product label (ScourGuard 3® (K)/C, lot #149398170 manufactured by SmithKline Beecham Animal Health). Two thirds of the remainder of the cows were vaccinated with a 2 ml dose, subcutaneously, 8 weeks prior to calving with a combination vaccine including rotavirus, coronavirus, *Cl. perfringens* and *E. coli* fractions ("VP-916"). One third of that group, the 2 dose vaccinate group, received a second dose 6 weeks thereafter of a vaccine including only the rotavirus fraction ("VP-919."). The remainder of the cows were designated as controls and received a single 2 ml dose of a combination vaccine including coronavirus and bacterin fractions ("VP-917").

Antibacterial treatment was performed as described supra.

Prior to calving all cows were pastured together. Upon calving, cow-calf pairs were separated from the herd. After challenge, the pairs were isolated to prevent "nose-to-nose" contact for approximately 12–24 hours, after which the pairs were moved to test pens for the remainder of the study. Twenty-one days post challenge, the pairs were moved to off-test pens.

Challenge material was a field strain of bovine rotavirus harvested from a 4 day old colostrum deprived Angus calf. Rotavirus presence was detected with a Rotazyme II test kit (Abbot Laboratories). Virus isolation testing on MA104 cells was positive for rotavirus. The titer of the challenge material was $10^{9.22}FAID_{50}/ml$ ±0.64. Rotavirus only was detected by Electron Microscopy. RNA-Page analysis identified the virus as Group A rotavirus and the specific P and G types of rotavirus were determined to be P1/P5 and G6/G8 genotypes.

After the above analysis, 5 ml of the rotavirus challenge material was diluted in 5 ml of MEM containing antibiotics, producing a 10 ml challenge dose. Calves were inoculated with the challenge dose at 3–12 hours post parturition. Two 1 ml doses were delivered intranasally and the remainder delivered orally. Subsequently, calves were monitored and assigned daily clinical scores for fecal consistency, dehydration and depression, as described supra. In addition, clinical scores from 0–3 were assigned for respiratory signs, where 0=normal and 3=dispense, and scores for death, where 0=live and 10=dead.

Fecal samples were obtained daily for 21 days as previously described herein. Additional fecal samples were collected, as described supra, on challenge days 0, 7, 14 and 21. Blood samples for serum and colostrum/milk samples were also collected, as previously described, at challenge days 0, 7, 14 and 21. Calves weights were monitored at birth and on challenge days 0, 7, 14 and 21.

Six heifers were removed from the study prior to second vaccination for various reasons, none of which effect the results of the study. Fourteen additional animals were removed from the study prior to challenge for various reasons, none of which effected the results of the study. Three calves were removed from the study after challenge for various reasons, none of which effected the results of the study.

Challenged control calves had softer than normal stools and began to show signs of dehydration as early as one day post challenge. Overall, the control calves had clinical scores 1.5 times higher than those of the calves from vaccinated heifers. Total clinical scores in calves born to vaccinated heifers were significantly lower (p=0.004) than those of the control calves. Both 2 dose and 1 dose vaccinates' scores were significantly lower than those of the control animals (p=0.006 and p=0.044, respectively). The average total clinical scores of challenged animals are summarized below in Table 2.

TABLE 2

| TREATMENT | AVERAGE TOTAL CLINICAL SCORE |
| --- | --- |
| Both vaccine groups | 25.79 |
| control | 39.76 |
| 2 vaccines | 21.60 |
| 1 vaccine | 26.53 |
| ScourGuard ® (K)/C | 47.33 |

Fecal consistency scores of control calves were 1.5 times higher than those of calves from vaccinated heifers. Total fecal consistency scores from calves of vaccinated dams were significantly lower (p=0.019) than those of control calves. Two dose vaccinates scores were also significantly different than the controls (p=0.011). However, 1 dose vaccinates' scores were not quite significant when compared to the controls (p=0.307).

The mortality rate in the control calves was 29%, with 60% of those calves being positive for rotavirus at necropsy, demonstrating clinical signs for 3–6 days prior to death and shedding virus while alive. Thirteen percent of the one dose vaccinate calves died, while 20% of the 2 dose vaccinate calves died.

No significant weight gain difference was exhibited among the test groups. Statistical evaluation for clinical scores, fecal consistency scores, weight gain and mortality rates are summarized below in Table 3.

TABLE 3

| | All Calves Analysis Of Variance | | |
| --- | --- | --- | --- |
| Test Group | Clinical Scores | Fecal Consistency Scores | Weight Day 21 |
| Both vaccines v. controls | 0.004 | 0.019 | 0.515 |
| 2 vaccines v. controls | 0.006 | 0.011 | 0.082 |
| 1 vaccine v. controls | 0.044 | 0.307 | 0.555 |
| ScourGuard ® (K)/C | 0.839 | 0.382 | 0.460 |

These data establish a minimum antigenic level of each strain of rotavirus of $10^7 FAID_{50}$ per 2 ml dose.

Although the uses of the present invention have been disclosed primarily with respect to cattle, in particular calves, this is not deemed to limit the scope of this invention. The present invention may be used in other fields of industry, e.g., alternate veterinary applications. The present invention is embodied in inactivated polyvalent veterinary vaccines having improved compositional characteristics and improved derivative products, particularly useful for conferring immunity to prevent neonatal scours both in pregnant cows and young calves. Regardless of the specific application of the instant invention, the methodology details are calculated according to protocols well known in the art, as well as those disclosed herein. Further, the refinement of said necessary calculations is routinely made by those of ordinary skill in the art and is within the ambit of tasks routinely performed by them without undue experimentation.

While the above description contains much specificity, these specificities should not be construed as limitations on the scope of the invention, but rather exemplification of the preferred embodiment thereof. That is to say, the foregoing description of the invention is exemplary for purposes of illustration and explanation. Without departing from the spirit and scope of this invention, one skilled in the art can make various changes and modification to the invention to adapt it to different usages and conditions. As such, these changes and modification are properly, equitably and intended to be within the full range of equivalence of the following claims. Thus, the scope of the invention should be determined by the appended claims and their legal equivalents, rather than by the examples provided herein.

We claim:

1. A combination bovine rotavirus and coronavirus vaccine capable of inducing immunity in bovine animals without serious side effects, the combination vaccine comprising a vaccinal amount of a plurality of inactivated bovine rotavirus strains, at least one inactivated bovine coronavirus strain, and at least one vaccinal bacteria.

2. The combination vaccine of claim 1, wherein said rotavirus strains comprise Cody 81-4 having ATCC accession number PTA-5955, G type 10 B223 having ATCC accession number PTA-5956 and B641 having ATCC accession number PTA-5957 and the coronavirus strain comprises the Mebus strain having ATCC accession no. VR-874.

3. The combination vaccine of claim 2, wherein said vaccinal bacteria comprise a vaccinal amount of a plurality of *Escherichia coli* bacterin strains and at least one *Clostridium perfringens* Type C bacterin strain.

4. The combination vaccine of claim 3, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

5. The combination vaccine of claim 3, wherein said *Cl. perfringens* bacterin strain comprises GL47 having ATCC accession no. PTA-3000.

6. The combination vaccine of claim 3, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953 and said *Clostridium perfringens* bacterin strain comprises GL47 having ATCC accession no. PTA-3000.

7. The combination vaccine of claim 2 wherein said vaccinal bacteria comprises a vaccinal amount of a plurality of *Escherichia coli* bacterin strains.

8. The combination vaccine of claim 7, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

9. The combination vaccine of claim 2 wherein said vaccinal bacteria comprises a vaccinal amount of at least one *Clostridium perfringens* Type C bacterin strain.

10. The combination vaccine of claim 9, wherein said *Clostridium perfringens* bacterin strain comprises GL47 having ATCC accession no. PTA-3000.

11. The combination vaccine of claim 1 wherein said rotavirus strains comprise Cody 81-4 having ATCC accession number PTA-5955, G type 10B223 having ATCC accession number PTA-5956 and B641 having ATCC accession number PTA-5957.

12. The combination vaccine of claim 11 wherein said vaccinal bacteria comprises a vaccinal amount of a plurality of *Escherichia coli* bacterin strains.

13. The combination vaccine of claim 12, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

14. The combination vaccine of claim 11 wherein said vaccinal bacteria comprises a vaccinal amount of at least one *Clostridium perfringens* Type C bacterin strain.

15. The combination vaccine of claim 14, wherein said *Clostridium perfringens* bacterin strain comprises GL47 having ATCC accession no. PTA-3000.

16. The combination vaccine of claim 1, wherein said vaccinal bacteria comprise a vaccinal amount of a plurality of *Escherichia coli* bacterin strains and at least one *Clostridium perfringens* Type C bacterin strain.

17. The combination vaccine of claim 16, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

18. The combination vaccine of claim 16, wherein said *Clostridium perfringens* bacterin strain comprises GL47 having ATCC accession no. PTA-3000.

19. The combination vaccine of claim 16, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953 and said *Clostridium perfringens* bacterin strain comprises GL47 having ATCC accession no. PTA-3000.

20. The combination vaccine of claim 1 wherein said vaccinal bacteria comprises a vaccinal amount of a plurality of *Escherichia coli* bacterin strains.

21. The combination vaccine of claim 20, wherein said *Escherichia coil* bacterin strains comprise B41 having ATCC accession number PTA-5951, B42 having ATCC accession number PTA-5952, B44 having ATCC accession number PTA-5954, and B117 having ATCC accession number PTA-5953.

22. The combination vaccine of claim 1 wherein said vaccinal bacteria comprises a vaccinal amount of at least one *Clostridium perfringens* Type C bacterin strain.

23. The combination vaccine of claim 22, wherein said *Clostridium perfringens* bacterin strain comprises GL47 having ATCC accession no. PTA-3000.

24. The combination vaccine of claim 1 wherein said the coronavirus strain comprises the Mebus strain having ATCC accession no. VR-874.

25. The combination vaccine of claim 24 wherein said vaccinal bacteria comprises a vaccinal amount of a plurality of *Escherichia coli* bacterin strains.

26. The combination vaccine of claim 25, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

27. The combination vaccine of claim 24 wherein said vaccinal bacteria comprises a vaccinal amount of at least one *Clostridium perfringens* Type C bacterin strain.

28. The combination vaccine of claim 27, wherein said *Clostridium perfringens* bacterin strain comprises GL47 having ATCC accession no. PTA-3000.

29. The combination vaccine of claim 1, 2, 16, 3–6, or 20–28, wherein the virus is inactivated with an inactivating agent selected from beta-propiolactone, formalin, ethyleneimine derivatives, UV radiation and heat.

30. The vaccine of claim 29, wherein said inactivating agent is beta-propiolactone.

31. The vaccine of claim 29, wherein said inactivating agent comprises β-propiolactone and said adjuvant comprises an oil based adjuvant.

32. The combination vaccine of claim 1, 2, 16, 3–6, or 20–28 further comprising an adjuvant, wherein the adjuvant is selected from oil based adjuvants, Freund's incomplete, alginate, aluminum hydroxide gel and potassium alum.

33. The vaccine of claim 32, wherein the adjuvant is an oil based adjuvant.

34. The vaccine of claim 32, wherein said inactivating agent comprises β-propiolactone and said adjuvant comprises an oil based adjuvant.

35. A method of inducing scours immunity in neonatal bovine animals without serious side effect comprising the steps of administering the combination vaccine of claims 1, 2, 16, 3–6 or 20–28 to pregnant cows prior to calving.

36. The method of claim 35, further comprising administering a second dose of the combination vaccine to pregnant cows prior to calving.

37. A method of vaccinating bovine animals comprising administering parenterally to said animals the combination vaccine of claim 1, 2, 16, 3, 19, or 6.

38. The method of claim 37, wherein the vaccine is administered by intramuscular injection.

39. The method of claim 37, wherein the vaccine is administered by subcutaneous injection.

40. A method of vaccinating bovine animals comprising administering parenterally to said animals a combination bovine rotavirus and bovine coronavirus vaccine capable of inducing immunity in bovine animals without serious side effect, the combination vaccine comprising a vaccinal amount of a plurality of inactivated bovine rotavirus strains, at least one inactivated bovine coronavirus strain, and at least one vaccinal bacteria.

41. The method of claim 40, wherein said vaccinal bacteria comprise a vaccinal amount of a plurality of *Escherichia coli* bacterin strains and at least one *Clostridium perfringens* Type C bacterin strain.

42. The method of claim 41, wherein the *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

43. The method of claim 41, wherein the *Clostridium perfringens* bacterin strain comprises GL47 having ATCC accession no. PTA-3000.

44. The method of claim 41, wherein the *Escherichia coil* bacterin strains comprise B41 having ATCC accession number PTA-5951, B42 having ATCC accession number PTA-5952, B44 having ATCC accession number PTA-5954, and B117 having ATCC accession number PTA-5953 and the *Clostridium perfringens* bacterin strain comprises a GL47 having ATCC accession no. PTA-3000.

45. The method of claim 40, wherein said rotavirus strains comprise Cody 81-4 having ATCC accession number PTA-5955, G type 10B223 having ATCC accession number PTA-5956 and B641 having ATCC accession number PTA-5957.

46. The method of claim 45, wherein said vaccinal bacteria comprise a vaccinal amount of a plurality of *Escherichia coli* bacterin strains.

47. The method of claim 46, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

48. The method of claim 45, wherein said vaccinal bacteria comprise a vaccinal amount of at least one *Clostridium perfringens* Type C bacterin strain.

49. The method of claim 48, wherein said *Clostridium perfringens* bacterin strain comprises GL47 having ATCC accession no. PTA-3000.

50. The method of claim 40, wherein the coronavirus strain comprises the Mebus strain having ATCC accession no. VR-874.

51. The method of claim 50, wherein said vaccinal bacteria comprise a vaccinal amount of a plurality of *Escherichia coli* bacterin strains.

52. The method of claim 51, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

53. The method of claim 50, wherein said vaccinal bacteria comprise a vaccinal amount of at least one *Clostridium perfringens* Type C bacterin strain.

54. The method of claim 53, wherein said *Clostridium perfringens* bacterin strain comprises GL47 having ATCC accession no. PTA-3000.

55. The method of claim 40, wherein said vaccinal bacteria comprise a vaccinal amount of a plurality of *Escherichia coli* bacterin strains.

56. The method of claim 55, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

57. The method of claim 40, wherein said vaccinal bacteria comprise a vaccinal amount of at least one *Clostridium perfringens* Type C bacterin strain.

58. The method of claim 57, wherein said *Clostridium perfringens* bacterin strain comprises GL47 having ATCC accession no. PTA-3000.

59. The method of claim 40, wherein the rotavirus strains comprise Cody 81-4 having ATCC accession number PTA-5955, G type 10B223 having ATCC accession number PTA-5956 and B641 having ATCC accession number PTA-5957 and the coronavirus strain comprises the Mebus strain having ATCC accession no. VR-874.

60. The method of claim 59, wherein said vaccinal bacteria comprise a vaccinal amount of a plurality of *Escherichia coli* bacterin strains.

61. The method of claim 60, wherein said *Escherichia coli* bacterin strains comprise B41 having ATCC accession number PTA-5951, B42 having ATCC accession number PTA-5952, B44 having ATCC accession number PTA-5954, and B117 having ATCC accession number PTA-5953.

62. The method of claim 59, wherein said vaccinal bacteria comprise a vaccinal amount of at least one *Clostridium perfringens* Type C bacterin strain.

63. The method of claim 62, wherein said *Clostridium perfringens* bacterin strain comprises GL47 having ATCC accession no. PTA-3000.

64. The method of claim 40, 41, 45–44 or 55–54, wherein the vaccine is administered by intramuscular injection.

65. The method of claim 40, 41, 45–44 or 55–54, wherein the vaccine is administered by subcutaneous injection.

* * * * *